United States Patent [19]

Huchette et al.

[11] 4,390,523

[45] Jun. 28, 1983

[54] SORBOSE FOR INHIBITING FERMENTATION ACIDS IN THE MOUTH

[75] Inventors: Michel Huchette; Patrick Leroy, both of Lestrem, France

[73] Assignee: Roquette Freres, France

[21] Appl. No.: 109,512

[22] Filed: Jan. 4, 1980

Related U.S. Application Data

[63] Continuation of Ser. No. 838,833, Oct. 3, 1977, abandoned, which is a continuation of Ser. No. 678,236, Apr. 19, 1976, abandoned, which is a continuation of Ser. No. 534,558, Dec. 19, 1974, abandoned, which is a continuation of Ser. No. 400,017, Sep. 24, 1973, abandoned.

[30] Foreign Application Priority Data

Sep. 26, 1972 [FR] France .............................. 72.34057

[51] Int. Cl.³ ...................... A61K 9/68; A61K 31/70
[52] U.S. Cl. ........................................ 424/48; 424/49; 424/180; 426/3; 426/658
[58] Field of Search ........................... 424/180, 49, 48; 426/804, 568, 660, 658, 3

[56] References Cited

U.S. PATENT DOCUMENTS 3,278,314 10/1966 Colby et al. .................... 426/658

OTHER PUBLICATIONS

"The Merck Index", Eighth Ed., 1968, p. 972.
Muhlemann et al., "Reprint From Helv. Odont. Acta." vol. 19, #76, 1975.

*Primary Examiner*—Johnnie R. Brown
*Attorney, Agent, or Firm*—Larson and Taylor

[57] ABSTRACT

Substitute for sugar, i.e. for saccharose, said substitute being constituted by sorbose.

1 Claim, No Drawings

SORBOSE FOR INHIBITING FERMENTATION ACIDS IN THE MOUTH

This is a continuation of application Ser. No. 838,833, filed Oct. 3, 1977, which is a continuation of Ser. No. 678,236, filed Apr. 19, 1976, which is a continuation of Ser. No. 534,558, filed Dec. 19, 1974, which is a continuation of Ser. No. 400,017, filed Sept. 24, 1973, all of which applications are now abandoned.

The invention relates to a substitute for sugar, it being understood that it is saccharose that is designated by this term.

Sugar substitutes are acquiring an ever-increasing importance in the dietary foods and low-calories type foods industry. Due to them, it is possible to eliminate sugar to a large degree from the food of diabetics as well as that of persons who must keep a slimming or reducing diet.

It is useful to recall moreover that sugar has cariogenic properties from which the substitutes will preferably also be free.

Certain substances have already been proposed as sugar substitutes.

Although in general these known products are satisfactory on the plane of sweetening power, they present disadvantages which are not to be disregarded.

Thus, saccharin, one of the best-known sugar substitutes, has the disadvantage of producing an unpleasant aftertaste for the consumer; the polyols derived from sugars, such as sorbitol, mannitol and xylitol, are laxative in high doses, and as regards levulose it is very hydroscopic.

Finally, other substitutes, for example the cyclamates, are the subject of serious reservations on the part of the medical profession in regards to their harmfulness.

The object of the invention is, above all to provide a sugar substitute which, while giving satisfaction on the plane of sweetening power, complies with the desiderata both of the medical profession and of the consumer better than those substitutes already in existence.

The applicant company has found that sorbose satisfies these various criteria.

Consequently, the sugar substitute according to the invention is constituted by sorbose.

The invention therefore relates to the application of sorbose to the manufacture of foods of all kinds, in particular dietetic foods, foods for diabetics, confectionery and others, and also to the manufacture of medicaments.

It can, in any case, be clearly understood with the aid of the additional description which follows and of the accompanying Examples.

The applicant company has been able to show, at the end of many tests, that sorbose is devoid of toxicity, does not modify true glycemia, does not give rise to the formation of acids or to a lowering of the pH by fermentation under the action of oral bacteria, and has satisfactory sweetening and organoleptic properties.

Sorbose is a carbohydrate of the family of the ketohexoses its empirical formula being $C_6H_{12}O_6$ and its molecular weight being 180.

It is a sugar rather soluble in water, but not very soluble in alcohol, which possesses an agreeable taste and has a sweetening power comparable to that of saccharose.

Sorbose is obtained by fermentation of sorbitol by bacteria of the Acetobacter family, in particular *Acetobacter suboxydans*. This fermentation is described in numerous publications. Sorbose moreover constitutes at present one of the intermediate stages in the industrial synthesis of ascorbic acid or vitamin C.

The toxicity of sorbose has been studied in a first series of tests.

The test animals were ROCKFELLER mice and WISTAR rats.

These tests have enabled it to be ascertained that sorbose is a product devoid of acute, subacute and chronic toxicity, that it is tolerated perfectly on the clinical and biological planes, and that it does not result in any histologically detectable visceral lesion after prolonged administration orally and in high doses.

Thus, solutes of sorbose (concentrations used: 615, 700, 900, 1000 and 1100 mg per ml) were administered orally, intravenously and intraperitoneally in different doses and concentrations to male mice of the ROCKFELLER type and to male rats of the WISTAR type.

Orally, no lethalness was observed with a dose of 11 grams per kg of body weight in the case of the rats and with a dose of 27.5 grams per kg of body weight in the case of the mice.

Intravenously, no lethalness was observed with a dose of 5.5 grams per kg of body weight in the case of the rats and with a dose of 10 grams per kg of body weight in the case of the mice.

The application of the conventional Karber and Behrens method (described in Arch. Exp. Pharm. 1935—177—379-388) enabled the lethal dose 50 ($LD_{50}$) to be located intraperitoneally at 12.8 grams per kg of body weight in rats and 13.6 grams per kg of body weight in mice.

The high values found demonstrate the absence of acute toxicity in sorbose.

The food value of sorbose has been studied in a second series of tests.

Thus, sorbose was administered orally to rats of the WISTAR type, as a supplement to the usual food ration, in a dose of 0.330 grams per 100 grams of body weight; such a dose would correspond to a daily intake of 198 grams of sorbose in a 60 kg man. This test was carried on for four weeks and three months. Each morning, 1 milliliter per 100 grams of body weight of a sorbose solute in water containing 0.330 g/ml was administered orally to each of the animals.

During the period of the test, no clinically detectable anomalies were observed: the bahaviour, general condition and motility of the animals and the volume and rhythm of the daily ingestions or intakes of foods or drinking water were normal, as was the diuresis.

A progressive weight development comparable to that observed in control animals which did not receive sorbose was observed; it appears, therefore, that sorbose has no food value.

In the course of this experiment, detailed biological examinations concerning the urine and blood were carried out.

The urine examinations comprised the following:

determination of the reducing power (copper-neocuproin method), determination of the true glycosuria (glucose-oxydase method), determination of the proteinuria, measurement of the urinary pH, determination of the urinary ionogram relating to the chlorine ions, sodium and potassium.

These biological examinations were carried out first on animals fed normally and then on the same animals in the course of the following weeks during which sorbose was being administered as a supplement to the food ration, as hereinbefore described.

The results, assembled in Table I following, were recorded before and then after ingestion of sorbose.

The examinations of the blood comprised the following:

determination of the true glycemia (glucose-oxydase dosage), determination of the ionemia (chlorides-phosphates-bicarbonates-sodium-potassium), azotemia, proteinemia, albuminemia, calcemia, cholesterolemia, uricemia

TABLE I

Urinary biological parameters before and during oral administration of sorbose in a dose of 330 mg/100 g for 13 weeks.

| Rats Nos. | before ingestion of sorbose | | | | | | | after ingestion of sorbose | | | | | |
|---|---|---|---|---|---|---|---|---|---|---|---|---|---|
| | 1 | 2 | 3 | 4 | 5 | 6 | | 1 | 2 | 3 | 4 | 5 | 6 |
| pH | 8.5 | 9 | 8.6 | 9.8 | 9.2 | 8.9 | b | 8.5 | 8.2 | 8.2 | 9.2 | 9.1 | 9.2 |
| | | | | | | | c | 9 | 8.5 | 8.8 | 9 | 9.1 | 8.8 |
| Chlorides meq/24 h | 0.47 | 0.37 | 0.69 | 0.13 | 0.60 | 0.80 | a | 0.10 | 0.62 | 0.80 | 0.13 | 0.27 | 0.80 |
| | | | | | | | b | 1.27 | 0.90 | 1.11 | 1.56 | 1.00 | 1.46 |
| | | | | | | | c | 0.92 | 0.79 | 0.70 | 0.90 | 1.08 | 0.76 |
| Sodium meq/24 h | 0.45 | 0.30 | 0.50 | 0.51 | 0.41 | 0.30 | a | 0.67 | 0.60 | 0.93 | 0.69 | 1.05 | 0.52 |
| | | | | | | | b | 0.72 | 0.72 | 0.79 | 0.97 | 1.46 | 0.79 |
| | | | | | | | c | 0.39 | 0.34 | 0.54 | 0.45 | 0.46 | 0.61 |
| Potassium meq/24 h | 1.05 | 0.96 | 1.32 | 1.00 | 0.86 | 0.73 | a | 1.10 | 1.03 | 1.68 | 1.26 | 1.48 | 1 |
| | | | | | | | b | 1.73 | 1.55 | 1.71 | 1.69 | 3 | 1.35 |
| | | | | | | | c | 1.19 | 0.99 | 1.20 | 1.26 | 1.20 | 1.08 |
| Proteins mg/24 h | 3.6 | 4.1 | 7.1 | 10.2 | 5.2 | 8.6 | a | 2.1 | 5.4 | 4.4 | 4.7 | 6.8 | 3.6 |
| | | | | | | | b | 3.7 | 1.6 | 3.6 | 2.5 | 2.2 | 1.1 |
| | | | | | | | c | 1.3 | 2.4 | 2.5 | 2.8 | 3.2 | 2.2 |
| Total Reducing Power mg/24 h | 15 | 13 | 10 | 11 | 19 | 14 | a | 56 | 30 | 39 | 38 | 35 | 28 |
| | | | | | | | b | 33 | 17 | 20 | 32 | 54 | 41 |
| | | | | | | | c | 36 | 31 | 32 | 41 | 31 | 32 |
| Glycosuria | No glycosuria was detected either before or during the administration of the sorbose. | | | | | | | | | | | | | a = first week
b = fifth week
c = thirteenth week

Examination of the foregoing Table enables it to be established that in the case of the WISTAR rat:

sorbose causes the appearance of the reducing power in the urine, but does not result in true glycosuria, sorbose does not lead to a significant modification of the physiological proteinuria, sorbose does not modify the urinary pH, sorbose does not modify the urinary ionogram.

Chromatographic examination of the urine of animals ingesting sorbose confirms the absence of glucose and the presence of sorbose, whereas neither glucose nor sorbose is found in the urine of animals not ingesting sorbose.

and creatinemia, the total bilirubinemia and the levels of the alkaline phosphatases, the creatine-phosphokinases and the glutamino-oxaloacetic transaminases (these determinations were effected with the aid of a Technicon SM A 6+SM A 12 autoanalyzer).

These biological tests were carried out first on animals fed normally and then on the same animals in the course of the following weeks during which sorbose was being administered as a supplement to the food ration, as hereinbefore described.

The biological parameters assembled in Table II following were recorded before and then after ingestion of sorbose.

TABLE II

Biological parameters of blood before and during oral administration of sorbose in a dose of 330 mg/100 g for 13 weeks.

| Rats Nos. | before ingestion of sorbose | | | | | | after ingestion of sorbose | | | | | |
|---|---|---|---|---|---|---|---|---|---|---|---|---|
| | 1 | 2 | 3 | 4 | 5 | 6 | 1 | 2 | 3 | 4 | 5 | 6 |
| Cl meq/l | 103 | 106 | 105 | 103 | 105 | 107 | 105 | 107 | 106 | 106 | 103 | 105 |
| $HCO_3$ meq/l | 12 | 7.5 | 12 | 10 | 8 | 12 | 16 | 7.5 | 12 | 11.5 | 7.5 | 12.5 |
| $K^+$ meq/l | 6.1 | 7.1 | 6.3 | 6.9 | 7.2 | 6.5 | 6.5 | 6.2 | 7 | 7.1 | 8.5 | 7.5 |
| $Na^+$ meq/l | 141 | 143 | 143 | 142 | 144 | 141 | 145 | 147 | 142 | 142 | 141 | 143 |
| $Ca^{++}$ mg/l | 88 | 96 | 101 | 98 | 102 | 96 | 84 | 102 | 97 | 100 | 100 | 108 |
| Phosphates mg/l | 80 | 86 | 84 | 92 | 88 | 79 | 92 | 90 | 82 | 89 | 90 | 86 |
| Urea g/l | 0.44 | 0.54 | 0.36 | 0.51 | 0.50 | 0.55 | 0.74 | 0.62 | 0.50 | 0.60 | 0.60 | 0.70 |
| Proteins g/l | 70 | 65 | 68 | 64 | 71 | 80 | 62 | 62 | 65 | 64 | 64 | 72 |
| Albumin g/l | 27 | 28 | 26 | 27 | 27 | 27 | 28 | 26 | 30 | 27 | 27 | 28 |
| Cholesterol g/l | 0.80 | 1.20 | 0.85 | 1.15 | 1.10 | 1.45 | 0.30 | 0.80 | 0.80 | 1.10 | 1.10 | 1.30 |
| Uric acid g/l | 28 | 40 | 39 | 41 | 45 | 62 | 26 | 38 | 29 | 30 | 38 | 44 |
| Creatine mg/l | 13 | 14 | 15 | 15 | 14 | — | 18 | 14 | 16 | 16 | 16 | 15 |
| Total bilirubin m/l | 4 | 4 | 4 | 4 | 4 | — | 4 | 4 | 4 | 4 | 4 | 4 |
| Alkaline phosphates | 60 | 100 | 65 | 75 | 105 | 115 | 50 | 110 | 60 | 80 | 100 | 100 |

TABLE II-continued

Biological parameters of blood before and during oral administration of sorbose in a dose of 330 mg/100 g for 13 weeks.

| Rats Nos. | before ingestion of sorbose | | | | | | after ingestion of sorbose | | | | | |
|---|---|---|---|---|---|---|---|---|---|---|---|---|
| | 1 | 2 | 3 | 4 | 5 | 6 | | 1 | 2 | 3 | 4 | 5 | 6 |
| (IU mU/ml) C.P.K. IU | 50 | 60 | 60 | 50 | 60 | — | | 50 | 50 | 60 | 60 | 60 | 50 |
| (mU/ml) S G O T IU (mU/ml) | 340 | 420 | 370 | 410 | 360 | — | | 390 | — | 360 | 370 | 470 | — |
| Total reducing power in g/l | 1.20 | 1.20 | 1.25 | 1.25 | 1.15 | 1.25 | a | 1.18 | 1.20 | 1.20 | 1.25 | 1.18 | 1.25 |
| | | | | | | | b | 1.15 | 1.10 | 1.20 | 1.15 | 1.10 | 1.10 |
| | | | | | | | c | 1.20 | 0.75 | 1.40 | 1.35 | 1.35 | 1.30 |
| Glycemia in g/l | 0.92 | 1.17 | 1.15 | 1.15 | 1.15 | 1.15 | a | 1.10 | 1.15 | 1.05 | 1.15 | 1.12 | 1.16 |
| | | | | | | | b | 1.05 | 1 | 1.05 | 0.95 | 0.95 | 0.90 |
| | | | | | | | c | 0.95 | 0.70 | 1.25 | 1.20 | 1.25 | 1.15 | a = 4th week
b = 10th week
c = 13th week
In Table II:
C.P.K. = creatine-phospho-kinase and
S G O T = seric-glutamino-oxaloacetic transaminase.

The results assembled in Table II enable it to be established that in the case of the tests relating to WISTAR rats the ingestion of sorbose does not modify the value of the true glycemia or that of the total reducing power of the serum and does not modify the serobiogram.

The results of all these biological analyses enable sorbose to be considered as being a sugar which is tolerated perfectly.

At the end of the tests the animals were put to death so that anatomical and histopathological observations could be made. Although no anatomical anomaly was found on examination of the viscera, a histopathological study of certain vital organs, such as the stomach, the small intestine, the large intestine, the liver, the kidneys and the pancreas was undertaken. This did not enable any histopathological change of structure of the organs examined to be detected.

To complete the tests concerned with animals, tests were carried out for hypersorbemia produced in man (ingestion on an empty stomach in one lot of a dose of sorbose equivalent to 1 gram per kg of weight). It was found that the ingestion of such a massive dose of sorbose was, on the one hand, well tolerated and, on the other hand, caused a heightening of the total reducing power of the blood, which disappeared in a few hours, but did not produce any variation in the true glycemia.

The cariogenic power of the sorbose was likewise examined.

It will be recalled first of all, in connection with the etiology of dental caries, that the microorganisms of the mouth cause carbohydrates to ferment and produce enough acids at the tooth surface to attack and decalcify the enamel. One of the methods of preventing the commencement of decay is the use, for example in toothpastes, of substances inhibiting the development of the acidifying bacteria of the mouth and avoiding, at the same time, the formation of fermentation acids. Another possibility consists in replacing the carbohydrates customarily employed in the manufacture of food products, such as saccharose and glucose (which give rise to a lowering of the pH and a considerable production of acids under the action of the mouth bacteria), by products resisting the fermenting action of the mouth bacteria. It has been proposed to use for this purpose sorbitol, mannitol, dulcitol or hydrogenated hydrolysates of starch, such as the one known under the mark "Lycasin". These polyalcohols, however, although they have a sweet, fresh and pleasant taste, do not have sufficient sweetening power and are even laxative where some of them are concerned, as already indicated hereinbefore. Sorbose, however, which has a pronounced sweet taste comparable to that of saccharose, does not lead, by fermentation by bacteria of the mouth, to the production of fermentation acids or to a lowering of the pH to the region of 5.0 to 5.5, which is usually regarded as being necessary for decalcification of the enamel.

To demonstrate these non-cariogenic properties of sorbose the following tests were carried out.

A series of tubes containing 10 ml of a sugarless nutritive culture medium at pH 7 was prepared. These tubes were sterilized by passing them through an autoclave at 120° C. for 20 minutes.

1 ml of sterile water was introduced into a first series of five tubes to make a control series.

1 ml of a sterile 18% solution of dextrose (weight-/volume=W/V) was introduced into a second series of five tubes.

1 ml of a sterile 18% solution of saccharose (W/V) was introduced into a third series of five tubes.

1 ml of a sterile 18% solution of sorbose (W/V) was introduced into a fourth series of five tubes.

The sterile solutions of dextrose, saccharose and sorbose were obtained by sterilizing filtration by the usual technique.

A dilution of human saliva was prepared for immediate use and four tubes of each series were inoculated with the same volume of dilute saliva.

The formation of acids was followed by electric measurement of the pH and by determination of the quantity of acids formed; this determination was effected with a N/40 sodium/hydroxide solution, phenolphthalein being used as a neutralization indicator; a first determination was made before incubation, the following four determinations after incubations of 3, 6, 10 and 24 hours, respectively, at 37° C.

The results are assembled in Table III (pH value and value of the number of ml of sodium hydroxide necessary for neutralization).

On examination of this Table it will be noted that:

in the sugarless medium, there is no formation of acids or considerable lowering of the pH, in the media containing glucose or saccharose, there is a distinct acidification and a lowering of the pH to values of 5.1 and 5.3, in the medium containing sorbose, there is no formation of acids or lowering of the pH (its development is practically that of the sugarless control medium).

TABLE III

| Medium | 0 hours | | 3 hours | | 6 hours | | 10 hours | | 24 hours | |
|---|---|---|---|---|---|---|---|---|---|---|
| | pH | NaOH in ml | pH | NaOH in ml | pH | NaOH in ml | pH | NaOH in ml | pH | NaOH in ml |
| Without sugar | 7.0 | 2.40 | 6.90 | 2.50 | 6.95 | 2.25 | 6.85 | 2.05 | 6.90 | 1.95 |
| With dextrose | 7.0 | 2.50 | 6.90 | 2.25 | 6.80 | 2.40 | 6.50 | 2.80 | 5.30 | 5.70 |
| With saccharose | 7.0 | 2.50 | 6.90 | 2.45 | 6.90 | 2.40 | 6.10 | 3.20 | 5.10 | 6.10 |
| With sorbose | 7.0 | 2.50 | 6.80 | 2.25 | 6.90 | 2.20 | 6.80 | 1.90 | 6.80 | 1.90 |

Sorbose is therefore a sugar which does not give rise to the formation of acids by oral bacteria and, consequently, a non-cariogenic sugar.

It is therefore possible, due to the properties which have just been illustrated by the foregoing tests, to employ sorbose to replace saccharose in the manufacture of food, dietetic, confectionery and other products, and also in the preparation of medicaments, in which it plays the role of excipient.

In these various products, sorbose may replace all or part, preferably the whole, of the saccharose which is customarily used.

The substitution of the sugar by equivalent quantities of sorbose is possible taking into account the fact that sorbose has substantially the same sweetening power as saccharose; it is emphasized that it is possible to use it also in combination with other sweetening products, such as glucose syrups, dextrose, sorbitol, mannitol, levulose or even with sweeteners such as the cyclamates and saccharin.

Among the aforesaid food products, in particular dietetic and confectionery products, there may be mentioned foods containing sugar and delicacies which are in solid, semi-solid or liquid form, for example baked foods such as biscuits and cakes, creams, ices, hard or soft caramels, sweets, confectionery in the form of gums, sugared almonds, pastilles, fruit dreams, chewing gum, effervescent powders, nougat, chocolates, jams and preserves, fondants, beverages such as soft drinks, syrups, fruit juices and other products.

To illustrate the foregoing, there are given hereinafter a certain number of Examples relating to food or pharmaceutical products in which, in accordance with the invention, sorbose replaces the saccharose.

EXAMPLE 1

Product for sweetening coffee, tea, milk and other liquid foods

Lumps of the aforesaid product were prepared by moistening sorbose with about 2% of water, a solvent or an aqueous solution of sorbose or of another sugar such as fructose, sorbitol or xylitol, pressing the sorbose into the form of parallelepipeds or cubes (with a weight of 1 to 5 g) and drying it in an oven.

EXAMPLE 2

Vitamin C tablets

Tablets of the following composition were prepared:

| | |
|---|---|
| Sorbose | 984 g |
| Ascorbic acid | 10 g |
| Oil of lemon | 1 g |
| Glycerol palmitostearate | 5 g |
| Total | 1000 g |

The ingredients were mixed and the mixture was compressed by the usual method in a reciprocating or rotary tablet making machine to obtain tablets of desired weight and shape.

EXAMPLE 3

Sweets

Sweets were prepared by replacing the sugar usually employed by sorbose.

To do this, 50 parts of sorbose and 50 parts of sorbitol were mixed with the necessary amount of water and flavouring.

The paste obtained in this way was baked with a naked flame at 150° C. until dry.

EXAMPLE 4

Fruit cream or paste

A fruit cream of the following composition was prepared:

| | |
|---|---|
| Pectin | 17 g |
| Sorbose | 150 g |
| Water | 285 g |
| Apricot pulp | 75 g |
| Hydrogenated glucose syrup (for example the syrup known under the mark LYCASIN) | 750 g |
| Citric acid (50% solution) | 5 ml |

The pectin was mixed dry with 50 g of sorbose and the mixture was poured into water brought to a temperature of 50. After swelling, the mixture was brought to boiling and the fruit pulp, the remainder of the sorbose and the hydrogenate glucose syrup were added. After concentration to 80° brix, the citric acid was added and the cream was poured into moulds.

EXAMPLE 5

Candying of confectionery goods

Fruit creams according to Example 4 were coated with crystallized sorbose.

EXAMPLE 6

Effervescent powder

An effervescent powder of the following formula was prepared:

| | |
|---|---|
| Sorbose | 455 g |
| Citric acid | 25 g |
| Sodium carbonate | 18 g |
| Flavouring (orange, lemon) | 2 g |

10 g of this powder was poured into tight sachets and these were sealed. The contents of the preparation were suitable for making a glass of soft drink.

EXAMPLE 7

Jam

To prepare an apricot jam, 300 g of sorbose, 200 g of hydrogenated glucose syrup of the LYCASIN brand were mixed.

This mixture was concentrated to 66° brix.

400 g of apricots were added to 350 g of the syrup obtained in this way and the mixture was boiled slowly.

As is obvious and is moreover already apparent from the foregoing, the invention is by no means limited to those modes of application and embodiments thereof which have been more particularly considered; on the contrary, it covers all variants thereof.

We claim:

1. In a method of inhibiting the production of fermentation acids in the mouth and the subsequent lowering of the pH to 5.0 to 5.5 that occurs during use of chewing gum by the fermentation of oral bacteria of sucrose contained in said chewing gum as a sweetening agent, the improvement comprising substituting sorbose for said sucrose.

* * * * *